United States Patent [19]
Tanaglia et al.

[11] Patent Number: 5,773,539
[45] Date of Patent: Jun. 30, 1998

[54] CATALYTIC COMPONENT BASED ON VANADIUM AND ITS USE IN THE PREPARATION OF EP(D)M

[75] Inventors: Tiziano Tanaglia, Bologna; Silvia Previati, Ferrara; Luigi Abis, Novara; Liliana Gila, Cameriano, all of Italy

[73] Assignee: Enichem Elastomeri S.r.l., Milan, Italy

[21] Appl. No.: 782,294

[22] Filed: Jan. 15, 1997

[30] Foreign Application Priority Data

Feb. 16, 1996 [IT] Italy .................................. MI96/A294

[51] Int. Cl.⁶ ..................................................... C08F 4/68
[52] U.S. Cl. .......................... 526/169.2; 556/42; 502/152
[58] Field of Search ........................... 556/42; 526/169.2; 502/152

[56] References Cited

U.S. PATENT DOCUMENTS 3,361,778  1/1968  Pedersen ................................ 260/429

FOREIGN PATENT DOCUMENTS 0 439 964  8/1991  European Pat. Off. ..
0 588 404  3/1994  European Pat. Off. ..
0 676 418  10/1995  European Pat. Off. ..

*Primary Examiner*—David W. Wu
*Attorney, Agent, or Firm*—Oblon, Spivak, McClelland, Maier & Neustadt, P.C.

[57] ABSTRACT

Catalytic component for the (co)polymerization of alpha-olefins consisting of the compound having the general formula $VL_3$, wherein V is trivalent vanadium and L is a ligand selected from those having general formula (I):

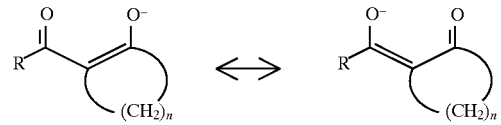

wherein R is selected from H and $C_1$–$C_{20}$ monofunctional hydrocarbyl radicals; n is an integer between 2 and 13 excluding 4 and 5.

14 Claims, No Drawings

CATALYTIC COMPONENT BASED ON VANADIUM AND ITS USE IN THE PREPARATION OF EP(D)M

The present invention relates to catalytic components and their use in the preparation of (co)polymers of alpha-olefins, particularly in the preparation of elastomeric ethylene-propylene (EPM) copolymers and ethylene-propylene-diene (EPDM) terpolymers.

It is known in literature that effective catalytic components for the (co)polymerization of alpha-olefins consist of organic compounds of Vanadium (in oxidation state 3 or 5) soluble in hydrocarbon solvents. Typical examples of the above organic compounds of Vanadium are:

Vanadyl trihalides, alkoxyhalides and alkoxides such as $VOCl_3$, $VOCl_2(OBu)$ and $VO(OC_2H_5)_3$;

Vanadium tetrahalides and Vanadium alkoxy halides such as $VCl_4$ and $VCl_3(OBu)$;

Vanadium and Vanadyl acetyl acetonates and chloro acetyl acetonates, such as $V(AcAc)_3$, $VOCl_2(AcAc)$, $VO(AcAc)_2$ wherein (AcAc) is an acetylacetonate;

Complexes between Vanadium halide and Lewis bases such as $VCl_3.2THF$ wherein THF is tetrahydrofuran.

The preferred Vanadium compound is V(III) acetyl acetonate.

The above Vanadium compounds are used in the presence of cocatalysts essentially consisting of organic compounds of Aluminium and optionally in the presence of halogenated promoters.

The Vanadium compounds of the prior art have the disadvantage however of an insufficient productivity.

New compounds of Vanadium soluble in hydrocarbon solvents have now been found which overcome the above inconveniences.

In accordance with this, the present invention relates to compounds of Vanadium having the general formula $VL_3$, wherein V is trivalent Vanadium and L is a ligand having general formula (I):

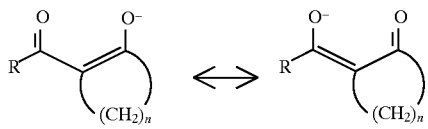

wherein R is selected from H and $C_1-C_{20}$ monofunctional hydrocarbyl radicals, it is preferably selected from H and $C_1-C_3$ hydrocarbyl radicals; n is an integer between 2 and 13 excluding 4 and 5, and is preferably selected from 2 and 3.

The compounds having general formula $VL_3$ which are most preferred are those selected from Vanadium (III) 2-acetyl cyclopentanoate and V(III) 2-formylcyclopentanoate, the preferred being V(III) 2-formylcyclopentanoate.

The complex having general formula $VL_3$ can be prepared by the reaction of a Vanadium (III) halide with the compound LH, i.e. with the ketone corresponding to the ligand having general formula (I), for example with 2-formylcyclopentanone or 2-acetylcyclopentanone.

A further object of the present invention relates to a process for the preparation of compounds having general formula $VL_3$ which comprises the reaction of a Vanadium (III) trihalide, preferably Vanadium (III) trichloride, with a cycloalkanone, excluding cyclohexanone and cycloheptanone, substituted in one of the alpha positions with respect to the ketone with an R—CO— radical, wherein R has the meaning defined above.

The reaction preferably takes place at a temperature of between 0° C. and 100° C.

In the preferred embodiment the V(III) trihalide and cycloalkanone are reacted (in an almost equimolar quantity) in water, an environment in which the $VL_3$ formed is practically insoluble. The $VL_3$ can be easily recovered by extraction with an organic solvent, for example toluene.

A further object of the present invention relates to a process for the preparation of elastomeric ethylene/alpha-olefin copolymers, preferably ethylenepropylene, and optionally a third dienic monomer, in suspension of liquid monomer, in the presence of a catalyst containing Vanadium and a cocatalyst basically consisting of an organic compound of Aluminium and optionally in the presence of a halogenated promoter, characterized in that the catalyst containing Vanadium is selected from those having general formula $VL_3$, wherein V is trivalent Vanadium and L is a ligand having general formula (I)

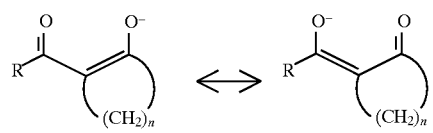

wherein R is selected from H and $C_1-C_{20}$ monofunctional hydrocarbyl radicals, and is preferably selected from H and $C_1-C_3$ hydrocarbyl radicals; n is an integer selected from between 2 and 3 or between 6 and 13, preferably between 2 and 3, and even more preferably 2.

The elastomeric copolymers which can be obtained with the process of the present invention contain from 35 to 85% by weight of ethylene, preferably from 45% to 75% by weight, and have an intrinsic viscosity, determined in o-dichlorobenzene at 135° C., of between 0.5 and 6 dl/g, preferably from 1 to 3 dl/g.

The term alpha-olefins refers to alpha-olefins having from 3 to 10 carbon atoms, for example propylene, butene-1, pentene-1, hexene-1; it is preferably however for the higher alpha-olefin to be propylene, thus obtaining the so-called EPM elastomeric copolymers.

As is known to experts in the field, ethylene and alpha-olefins can be copolymerized with other dienic monomers to give EPDM elastomeric terpolymers. In this case the content of diene must be less than 20%, preferably from 2 to 15%.

These termonomers can be selected from:

dienes with a linear chain such as 1,4-hexadiene and 1,6-octadiene;

acyclic dienes with a branched chain such as 5-methyl-1,4-hexadiene; 3,7-dimethyl-1,6-octadiene; 3,7-dimethyl-1,7-octadiene;

acyclic dienes with a single ring such as 1,4-cyclohexadiene; 1,5-cyclooctadiene; 1,5-cyclododecadiene;

dienes having bridge-linked alicyclic rings such as methyltetrahydroindene; dicyclopentadiene; bicyclo [2.2.2] hepta2,5-2,5-diene; alkenyl, alkylidene, cycloalkenyl and cycloalkylidene norbornenes such as 5-methylene-2-norbornene; 5-ethylidene-2-norbornene (ENB); 5-propenyl-2-norbornene.

Among the non-conjugated dienes typically used for preparing these copolymers, dienes containing at least a double bond in a stretched ring, are preferred, even more preferably 5-ethylidene-2-norbornene (ENB).

In the preparation process of elastomeric copolymers the compound $VL_3$ is used together with a cocatalyst selected from those having the general formula $R_nAlX_m$ wherein R is a $C_1$–$C_{20}$ alkyl radical, X is a halogen, m+n =3, m is an integer from 0 to 2.

Alkyl Aluminium chlorides such as $Al(C_2H_5)_2Cl$, $Al(C_2H_5)Cl_2$, are particularly useful, the most preferred being diethylaluminium chloride.

The molar ratio between cocatalyst and Vanadium can vary from 5 to 1000, preferably from 9 to 60.

In the copolymerization process in addition to the Vanadium compound of the present invention and the cocatalyst, it is preferable, as is known to experts in the field, to also use a catalysis promoter. These catalysis promoters normally belong to the group of chlorinated organic compounds, for example ethyl trichloroacetate, n-butyl perchlorocrotonate, diethyl dichloromalonate, carbon tetrachloride, chloroform. The molar ratio between promoter and Vanadium can vary from 0/1 to 1000/1, preferably from 0.5/1 to 40/1, even more preferably from 1/1 to 10/1.

The process of the present invention is carried out in solution or in suspension, preferably in suspension, in a reaction medium in which the polymer is substantially insoluble.

In the preferred embodiment the reaction medium prevalently consists of one of the comonomers, to which a saturated hydrocarbon, such as propane, butane, pentane, hexane or aromatics, preferably propane, is optionally added as diluent.

The polymerization temperature is maintained at a value of between –5° C. and 65° C., preferably from 25° C. to 50° C. The contact times vary from 10 minutes to 6 hours, preferably from 15 minutes to 1 hour.

The polymerization is generally carried out with hydrogen as moderator and molecular weight regulator, operating at a total pressure from 5 to 100 bars, preferably from 8 to 30 bars, with a ratio between partial ethylene pressure and partial hydrogen pressure of more than 4, preferably more than 20. Other compounds however, for example diethylzinc, can be used as molecular weight regulators.

The catalytic component of the present invention, under the same conditions, gives higher catalytic yields with respect to the catalytic components of the prior art, for example Vanadium (III) acetylacetonate.

The following examples provide a better understanding of the present invention.

EXAMPLES

All the reagents are commercial products; the solvents used in the polymerization and the promoters were deaerated under nitrogen and anhydrified on alumina and molecular sieves.

The organic compounds of aluminium were used in solution diluted in hexane.

The complexes of Vanadium were characterized by $^1$HNMR spectrum with a Bruker AM 300 spectrometer at room temperature. The samples were prepared by dissolving the compounds in deuterated toluene.

The signals observed, as a result of the paramagnetic nucleus of the Vanadium, are distributed over a region ranging from about 94 to 150 ppm.

The copolymers obtained in the following examples were characterized as follows:
A) The composition and product of the reactivity ratios ($r_1.r_2$) were determined by infra-red analysis of the polymer in the form of 0.2 mm thick films using an FTIR spectrophotometer of Perkin Elmer model 1760.

The propylene content was determined by measuring the ratio between the band absorbances at 4390 and 4255 cm$^{-1}$ and using a calibration curve calibrated with standard polymers.

The $r_1.r_2$ product was determined according to the spectroscopic method described in literature in *European Polymer Journal*, 4 pages 107–114 (1968).

The intrinsic viscosity was determined at 135° C. in o-dichlorobenzene.

Comparative Example 1 - Copolymerization of Ethylene and Propylene 900 ml of liquid propylene were charged into a perfectly anhydrous 1.7 dm$^3$ pressure-resistant reactor equipped with a propeller stirrer. The reactor is thermostat-regulated at 30° C. and saturated with ethylene until an overpressure of 5.4 bars is reached (corresponding to the composition in liquid phase indicated in table 1) and subsequently a further overpressure of 2 bars of hydrogen. The total pressure in the top of the reactor was 18.9 bars.

0.31 g of DEAC (diethylaluminium chloride) dissolved in hexane were then charged into the reactor followed by, in small portions, 0.02 grams of Vanadium (III) acetylacetonate and 0.072 g of n-butyl perchlorocrotonate (nBPCC) dissolved in toluene (corresponding to the quantity of vanadium indicated in table 1).

The reaction is carried out at a constant temperature, feeding the ethylene in continuous to keep the total pressure constant.

After 55 minutes, when the reaction had stopped, the monomers were evaporated and 152 g of copolymer were recovered and subsequently characterized (results in table 1).

Example 2
Preparation of V(fC5)$_3$, i.e. the compound having general formula VL$_3$ wherein L is 2-formylcyclopentanoate.
a) Preparation of the ligand 33 ml of ethyl formate and 44.7 ml of sodium methylate at 33% in methanol were added to 300 ml of anhydrous ethyl ether, under nitrogen.

The temperature was regulated at 0° C. and 23.1 ml of cyclopentanone were slowly added dropwise, care being taken that the temperature did not exceed 5° C., for 4 hours and then at room temperature for about 20 hours. The solid precipitate was filtered and then washed with anhydrous ether and again with heptane. About 20 grams of product were obtained.
b) Preparation of the Vanadium compound 8.7 grams of ligand previously prepared in step (a) are dissolved in 60 ml of water deaerated under nitrogen; 3.38 grams of Vanadium trichloride dissolved in 60 ml of deaerated water were then added slowly to this solution. 200 ml of toluene were added to the suspension formed, the toluene phase was then evaporated under vacuum obtaining 5.2 grams of product which upon analysis proved to be 11.4% of Vanadium.

The above Vanadium complex had the following $^1$HNMR spectrum: 94.81 ppm (1H), 93.95 ppm (1H), 85.02 ppm (1H), 83.80 ppm (1H), 82.96 ppm (2H), 74.97 ppm (2H), 1.32 ppm (1H), –0.68 ppm (1H), –0.87 ppm (1H), –1.20 ppm (1H), –1.35 ppm (1H), –1.56 ppm (1H), –1.70 ppm (1H), –1.97 ppm (1H), –2.0 ppm (1H), –3.15 ppm (1H), –6.46 ppm (1H), –8.76 ppm (1H), –9.36 ppm (1H), –14.0 ppm (1H), –16.34 ppm (1H), –18.54 ppm (1H), –136.36 ppm (1H), –140.50 ppm (1H), –143.52 ppm (1H), –148.65 ppm (1H).
c) Copolymerization of ethylene and propylene 900 ml of liquid propylene were charged into a perfectly anhydrous 1.7 dm$^3$ pressure-resistant reactor equipped with a propeller stirrer. The reactor is thermostat-regulated at 30° C. and saturated with ethylene until an overpressure of 5.4 bars is reached (corresponding to the composition in liquid phase indicated in table 1) and subsequently a further overpressure of 2 bars of hydrogen. The total pressure in the top of the reactor was 18.5 bars.

0.31 g of DEAC (Diethylaluminium chloride) dissolved in hexane were then charged into the reactor followed by, in small portions, 0.026 grams of V(fC5)$_3$ and 0.072 g of n-butyl perchlorocrotonate dissolved in toluene (corresponding to the quantity of vanadium indicated in table 1).

The reaction is carried out at a constant temperature, feeding the ethylene in continuous to keep the total pressure constant.

After 65 minutes, when the reaction had stopped, the monomers were evaporated and 168 g of copolymer were recovered and subsequently characterized (results in table 1).

Comparative Example 3 - Copolymerization of Ethylene and Propylene 900 ml of liquid propylene are charged into the pressure-resistant reactor described above. The reactor is thermostat-regulated at 35° C. and saturated with ethylene until an overpressure of 5.7 bars is reached (corresponding to the composition in liquid phase indicated in table 1) and subsequently a further overpressure of 2.2 bars of hydrogen. The total pressure in the top of the reactor was 21.6 bars.

Following the procedure described above (examples 1 and 2) 0.21 grams of DEAC dissolved in hexane and 0.072 grams of n-butyl perchlorocrotonate dissolved in toluene (corresponding to the quantity of Vanadium indicated in table 1), are charged into the reactor.

The reaction is carried out at a constant temperature, feeding the ethylene in continuous to keep the total pressure constant.

After 60 minutes, when the reaction had stopped, the monomers were evaporated and 110 g of copolymer were recovered and subsequently characterized (results in table 1).

Example 4 - Copolymerization of Ethylene and Propylene 900 ml of liquid propylene are charged into the pressure-resistant reactor described above. The reactor is thermostat-regulated at 35° C. and saturated with ethylene until an overpressure of 5.7 bars is reached (corresponding to the composition in liquid phase indicated in table 1) and subsequently a further overpressure of 1.8 bars of hydrogen. The total pressure in the top of the reactor was 20.8 bars.

0.31 grams of DEAC, 0.022 grams of V(fC5)$_3$ and 0.072 grams of n-butyl perchlorocrotonate dissolved in toluene (corresponding to the quantity of Vanadium indicated in table 1), were then charged into the reactor.

The reaction is carried out at a constant temperature, feeding the ethylene in continuous to keep the total pressure constant.

After 50 minutes, when the reaction had stopped, the monomers were evaporated and 118 g of copolymer were recovered and subsequently characterized (results in table 1).

Example 5 - Preparation of V(acC5)$_3$, i.e. VL$_3$ Wherein L is 2-acetylcyclopentanoate.

5.23 grams of sodium hydroxide were dissolved in 100 ml of water deaerated under nitrogen; 16.8 grams of 2-acetylcyclopentanone were then added to this solution, and then slowly 5.95 grams of Vanadium trichloride dissolved in 100 ml of deaerated water at 70° C. The suspension formed was then filtered under nitrogen washing with warm water. The precipitate was then extracted with toluene, and the toluene solution was then evaporated under vacuum obtaining 12 grams of product which upon analysis proved to be 11.15% of Vanadium.

The Vanadium complex thus prepared had the following $^1$HNMR spectrum: 75.1–74.20–73.62 ppm (8H), 50.14 ppm (3H), 49.80 ppm (3H), 48.43 ppm (6H), –1.21 (4H), –1.54 (4H), –4.91 ppm (1H), –5.34 ppm (1H), –5.75 ppm (1H), –6.28 ppm (1H), –6.62 ppm (1H), –7.07 ppm (1H), –7.49 ppm (1H), –7.94 ppm (1H).

Copolymerization of ethylene and propylene.

900 ml of liquid propylene are charged into the pressure-resistant reactor described above. The reactor is thermostat-regulated at 35° C. and saturated with ethylene until an overpressure of 5.7 bars is reached (corresponding to the composition in liquid phase indicated in table 1) and subsequently a further overpressure of 2.5 bars of hydrogen. The total pressure in the top of the reactor was 21.6 bars.

0.31 grams of DEAC dissolved in hexane, 0.026 grams of V(acC5)$_3$ and 0.0072 grams of n-butyl perchlorocrotonate dissolved in toluene (corresponding to the quantity of Vanadium indicated in table 1), were then charged into the reactor.

The reaction is carried out at a constant temperature, feeding the ethylene in continuous to keep the total pressure constant.

After 60 minutes, when the reaction had stopped, the monomers were evaporated and 127 g of copolymer were recovered and subsequently characterized (results in table 1).

Comparative Example 6

920 ml of liquid propylene are charged into the pressure-resistant reactor described above. The reactor is thermostat-regulated at 40° C. and saturated with ethylene until an overpressure of 6 bars is reached (corresponding to the composition in liquid phase indicated in table 1) and subsequently a further overpressure of 2 bars of hydrogen. The total pressure in the top of the reactor was 23.5 bars.

0.31 grams of DEAC dissolved in hexane and subsequently 0.02 grams of Vanadium (III) acetylacetonate and 0.072 grams of n-butyl perchlorocrotonate dissolved in toluene (corresponding to the quantity of Vanadium indicated in table 1), were then charged into the reactor.

The reaction is carried out at a constant temperature, feeding the ethylene in continuous to keep the total pressure constant.

After 45 minutes, when the reaction had stopped, the monomers were evaporated and 97 g of copolymer were recovered and subsequently characterized (results in table 1).

Example 7

1650 ml of liquid propylene are charged into the pressure-resistant reactor; the reactor is thermostat-regulated at 40° C. and saturated with ethylene until an overpressure of 6 bars is reached (corresponding to the composition in liquid phase indicated in table 1) and subsequently a further overpressure of 2 bars of hydrogen. The total pressure in the top of the reactor was 23.3 bars.

0.276 grams of DEAC dissolved in hexane and subsequently 0.0256 grams of V(fC5)$_3$ and 0.072 grams of n-butyl perchlorocrotonate dissolved in toluene (corresponding to the quantity of Vanadium indicated in table 1), were then charged into the reactor.

The reaction is carried out at a constant temperature, feeding the ethylene in continuous to keep the total pressure constant.

After 40 minutes, when the reaction had stopped, the monomers were evaporated and 128 g of copolymer were recovered and subsequently characterized (results in table 1).

Example 8

920 ml of liquid propylene are charged into the pressure-resistant reactor and the reactor is thermostat-regulated at 40° C.; it is saturated with ethylene until an overpressure of 6 bars is reached (corresponding to the composition in liquid phase indicated in table 1) and subsequently a further overpressure of 2 bars of hydrogen. The total pressure in the top of the reactor was 23.5 bars.

0.31 grams of DEAC, 0.026 grams of $V(acC5)_3$ and 0.072 grams of n-butyl perchlorocrotonate dissolved in toluene (corresponding to the quantity of Vanadium indicated in table 1), were then charged into the reactor.

The reaction is carried out at a constant temperature, feeding the ethylene in continuous to keep the total pressure constant.

After 50 minutes, when the reaction had stopped, the monomers were evaporated and 120 g of copolymer were recovered and subsequently characterized (results in table 1).

TABLE 1

| Ex. | Ethyl. % Liq. phase | Propyl. % Liq. phase | Tempera. °C. | DEAC mmol/l | nBPCC mmol/l | Vanadium mg | Cat. yield kg/gV | Propyl. % | $r_1 \cdot r_2$ | $[\eta]$ dl/g |
|---|---|---|---|---|---|---|---|---|---|---|
| 1 comp. | 12 | 88 | 30 | 2.6 | 0.23 | 2.92 | 52.1 | 29.3 | 0.3 | 1.6 |
| 2 | 12 | 88 | 30 | 2.6 | 0.23 | 2.96 | 56.8 | 29.6 | 0.5 | 1.57 |
| 3 comp. | 12 | 88 | 35 | 1.7 | 0.23 | 2.92 | 37.7 | 26.7 | 0.6 | 1.3 |
| 4 | 12 | 88 | 35 | 2.6 | 0.23 | 2.51 | 47.1 | 28.8 | 0.6 | 1.68 |
| 5 | 12 | 88 | 35 | 2.6 | 0.23 | 2.91 | 43.8 | 27.7 | 0.7 | 1.2 |
| 6 comp. | 12 | 88 | 40 | 2.6 | 0.23 | 2.92 | 33.4 | 26.4 | 0.6 | 1.24 |
| 7 | 12 | 88 | 40 | 1.3 | 0.13 | 2.92 | 43.8 | 28.8 | 1.1 | — |
| 8 | 12 | 88 | 40 | 2.6 | 0.23 | 2.91 | 41.4 | 26.6 | 0.5 | 1.46 |

We claim:

1. A compound of Vanadium having general formula $VL_3$, wherein V is trivalent Vanadium and L is a ligand having general formula (I)

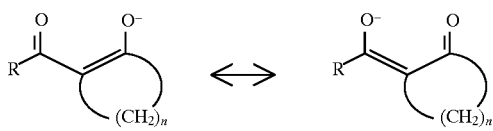

wherein R is selected from H or $C_1$–$C_{20}$ monofunctional hydrocarbyl radicals; n is an integer between 2 and 13 excluding 4 and 5.

2. The compound of Vanadium according to claim 1, wherein R is selected from H or $C_1$–$C_3$ hydrocarbyl radicals, n is an integer of 2 or 3.

3. The compound of Vanadium according to claim 2 wherein n=3, R is selected from H or $CH_3$.

4. A process for the preparation of a compound of Vanadium according to claim 1, which comprises reacting a Vanadium (III) trihalide with the compound LH wherein L has the meaning defined in claim 1.

5. The process according to claim 4, wherein the Vanadium (III) trihalide is Vanadium trichloride.

6. The process according to claim 4, wherein the compound LH is selected from 2-formylcyclopentanone or 2-acetylcyclopentanone.

7. A process for the preparation of elastomeric ethylene/alpha-olefin copolymers, and optionally a third dienic monomer, in a suspension of liquid monomer in the presence of a catalyst containing Vanadium and a cocatalyist consisting essentially of an organoaluminum compound and optionally in the presence of a halogenated promoter, characterized in that the catalyst containing Vanadium is selected from those having general formula $VL_3$, wherein V is trivalent Vanadium and L is a ligand having general formula (I)

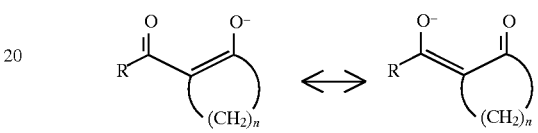

wherein R is selected from H or $C_1$–$C_{20}$ monofunctional hydrocarbyl radicals; n is an integer selected from between 2 and 13 excluding 4 and 5.

8. The process according to claim 7, wherein R is selected from H or $C_1$–$C_3$ hydrocarbyl radicals, n is an integer of 2 or 3.

9. The process according to claim 8, wherein n=3, R is selected from H or $CH_3$.

10. The process for the preparation of elastomeric copolymers according to claim 7, wherein the alpha-olefin is propylene.

11. The process according to claim 10, wherein the ethylene/propylene elastomeric copolymers have a content of ethylene of between 35 and 85% by weight.

12. The process according to claim 7, wherein the content of diene is less than 20%.

13. The process according to claim 12, wherein the content of diene is from 2 to 15%.

14. The process according to claim 10, wherein the ethylene/propylene elastomeric copolymers have a content of ethylene from 45 to 75% by weight.

* * * * *